United States Patent [19]

Schoedel

[11] Patent Number: 4,937,302

[45] Date of Patent: Jun. 26, 1990

[54] METHOD FOR SEPARATING METHANOL-METHYL METHACRYLATE MIXTURES

[75] Inventor: Ulrich Schoedel, Rossdorf, Fed. Rep. of Germany

[73] Assignee: Röhm GmbH, Darmstadt, Fed. Rep. of Germany

[21] Appl. No.: 295,653

[22] Filed: Jan. 10, 1989

[30] Foreign Application Priority Data

Feb. 5, 1988 [DE] Fed. Rep. of Germany ....... 3803406

[51] Int. Cl.$^5$ .................... C08F 2/06; C08F 120/14
[52] U.S. Cl. .................. 526/212; 526/329.7
[58] Field of Search .................. 526/329.7, 212

[56] References Cited

U.S. PATENT DOCUMENTS

| | | | |
|---|---|---|---|
| 2,072,904 | 3/1937 | Ries | 526/212 |
| 2,121,839 | 6/1938 | Strain | 526/212 |
| 2,135,443 | 11/1938 | Strain | 260/2 |
| 3,968,090 | 7/1976 | Shimada et al. | 526/329.7 |
| 4,149,984 | 4/1979 | Wenzel et al. | 252/51.5 A |
| 4,281,081 | 7/1981 | Jost et al. | 525/281 |
| 4,338,418 | 7/1982 | Jost et al. | 525/281 |

FOREIGN PATENT DOCUMENTS

| | | | |
|---|---|---|---|
| 0032175 | 7/1981 | European Pat. Off. | |
| 2455717 | 5/1975 | Fed. Rep. of Germany | 526/329.7 |
| 2740449 | 3/1979 | Fed. Rep. of Germany | |
| 2805826 | 8/1979 | Fed. Rep. of Germany | |
| 2940042 | 4/1981 | Fed. Rep. of Germany | 526/212 |
| 3211901 | 10/1983 | Fed. Rep. of Germany | |
| 37-7632 | 7/1962 | Japan | 526/329.7 |
| 50-19879 | 3/1975 | Japan | 526/329.7 |
| 59-213711 | 12/1984 | Japan | 526/329.7 |
| 61-108605 | 5/1986 | Japan | 526/329.7 |
| 418482 | 8/1974 | U.S.S.R. | 526/329.7 |
| 437284 | 10/1935 | United Kingdom | 526/329.7 |
| 475131 | 11/1937 | United Kingdom | 526/212 |
| 832319 | 4/1960 | United Kingdom | 526/329.7 |
| 1123722 | 8/1968 | United Kingdom | 526/329.7 |
| 1251737 | 10/1971 | United Kingdom | 526/329.7 |
| 1270292 | 4/1972 | United Kingdom | 526/329.7 |

OTHER PUBLICATIONS

Ullmann, Enzyclopaedie der technischen Chemie, 4th edition, vol. 16, p. 612.

*Primary Examiner*—Joseph L. Schofer
*Assistant Examiner*—N. Sarofim
*Attorney, Agent, or Firm*—Curtis, Morris & Safford

[57] ABSTRACT

A method for the separation of technical methanol-methyl methacrylate mixtures by polymerization of the methyl methacrylate, wherein the polymerization is suitably carried out as a copolymerization, at least with long-chain aliphatic $C_8$ to $C_{20}$-alkyl esters of methacrylic acid as comonomers, and as a solution polymerization, and the methanol can be recovered by distilling it off.

4 Claims, No Drawings

METHOD FOR SEPARATING METHANOL-METHYL METHACRYLATE MIXTURES

The present invention relates to a method for the separation of azeotrope-forming mixtures of methanol-methyl methacrylate by polymerization of the methyl methacrylate in suitable solvents and the recovery of methanol therefrom by distillation.

In the chemistry of methacrylates there are different technical processes which lead to the formation of mixture of methanol and methyl methacrylate. They arise in the esterification of methacrylic acid with methanol, but also in alcoholysis reactions with methyl methacrylate, i.e. in the reaction of the latter with alcohols to form other methacrylic acid esters. This latter method has considerable technical significance for the preparation of long-chain aliphatic methacrylic acid esters. The polymerized—usually copolymerized—esters of higher alcohols, particularly of alcohols having 12 to 18 C-atoms in the alkyl portion, are added to lubricating oils for lowering of the pour point and for improving the viscosity index (Ullmann, Encyklopädie der technischen Chemie, 4th edition, volume 16, page 612).

Methyl methacrylate and methanol form an azeotrope boiling at 1013 millibars at 64.2° C. which contains 84.5% of methanol. The working up of mixtures of methanol and methyl methacrylate by distillation leads to losses of methyl methacrylate and is uneconomical.

German patent publication DE-OS No. 32 11 901 describes a method for the separation of methanol from aqueous mixtures of methyl methacrylate and methanol, such as are formed in the esterification of methacrylic acid with methanol, in which are added to the mixture azeotrope-formers which, in the present of methyl methacrylate and water, form with methanol azeotropes which have a boiling point at least 0.2 Centigrade degrees below the boiling point of the azeotrope of methanol and methyl methacrylate.

These purely distillative, i.e. physical, measures make further method steps necessary for the separation of the new methanol-containing azeotrope which forms and the remaining methyl methacrylate-water mixture, since these two materials again form an azeotrope on further distillative separation.

Thus, the problem existed of finding a method for the separation of methanol-methyl methacrylate mixtures which would make possible a loss-free utilization of the valuable methyl methacrylate and a recovery of the free methanol.

According to the present invention, this problem is solved by polymerizing, and in particular copolymerizing, the methyl methacrylate in such a methanol-methyl methacrylate mixture and separating the methanol by distillation during or after the polymerization step. The method of the invention is particularly advantageous for the preparation of solution polymers. Particularly it has great technical and economic advantages for the preparation of lubricating oil additives comprising methacrylic acid esters.

The method of the invention is suitable for the separation of methanol-methyl methacrylate mixtures which, for example, contain 15 to 90 percent by weight of methanol. The method has particular significance for the separation of methanol and methyl methacrylate, with the simultaneous utilization of the latter as a polymerization component, present in methanol-methyl methacrylate mixtures such as arise in alcoholysis reactions. A technically important alcoholysis reaction is the earlier-mentioned preparation of long-chain aliphatic methacrylic acid esters. In this process, methanol-methyl methacrylate mixtures are formed containing 40 to 80 percent by weight of methanol and 60 to 20 percent by weight of methyl methacrylate, for example 65 percent by weight of methanol and 35 percent by weight of methyl methacrylate. These mixtures may possibly still also contain small amounts of water, e.g. 0.1 to 1 percent by weight.

It is known to polymerize methyl methacrylate in methanolic solution. In this way, a polymer precipitate is obtained, as described in U.S. Pat. No. 2,135,443. In the same patent, the polymerization of methyl methacrylate in hydrocarbons, such as in hexane or cyclohexane, is described, according to which the polymer is also insoluble in these solvents.

Thus, it is surprising that the use of technically produced methanol-methyl methacrylate mixtures such as are known from the alcoholysis reaction for the preparation of long-chain aliphatic $C_8$ to $C_{20}$-alkyl esters of methacrylic acid, for example, give no such polymer precipitates when polymerized in hydrocarbons for the preparation of lubricating oil additives which contain polymers of these long-chain methacrylic acid esters as essential components and which advantageously are used as copolymers with about 2 to 10 percent by weight of methyl methacrylate.

Such copolymers used as lubricating oil additives are inter alia described in DE-C No. 28 05 826, in EP-B No. 0,032,175, or in DE-C No. 27 40 449. They are prepared as solution polymers in petroleum oils and are added in this form to lubricating oils to adjust their viscosity-temperature behavior and their pour point. The pour point- and viscosity index- improvers comprising methacrylates often also contain olefin polymers (DE-C No. 27 40 449 and EP-B No. 0,032,175) or polymers having nitrogenous components, for example N-vinylimidazole (DE-C No. 28 05 826), particularly as graft polymers.

The present invention has as its object the separation of technical mixtures of methanol and methyl methacrylate by polymerization of the methyl methacrylate, particularly its copolymerization, at least with long-chain aliphatic $C_8$ to $C_{20}$ alkyl esters of methacrylic acid as comonomers, as a solution polymerization, and recovery of the methanol by distilling it off. Petroleum oils are advantageous as solvents.

By the method of the invention, complicated and loss-producing distillation methods are avoided in the working up of such methanol-methacrylate mixtures, such as are necessary at sites for the working up of methyl methacrylate, e.g. in its alcoholysis to higher esters and not in the neighborhood of a large technical plant for the preparation of methyl methacrylate. Also, the extensive and expensive means of transport to such large technical distillation installations are thus avoidable.

For example, in the preparation of a "Dobanol"-methacrylate ("Dobanol" is a synthetic alcohol of Shell having an average carbon number (C-number) of 13.2 to 13.8) by the alcoholysis of methyl methacrylate with "Dobanol" in the presence of basic catalysts, 100 kg of the long-chain ester and 20 kg of a methanol-methyl methacrylate mixture are formed as a distillate having the composition 65 percent by weight of methanol and 35 percent by weight of methyl methacrylate. By addition of the total distillate when polymerizing 100 kg of the "Dobanol"-methacrylate in petroleum oil, a polymer containing 6.5 percent by weight of copolymerized methyl methacrylate is obtained. For example as described in DE-C No. 28 05 826, the polymerization is carried out in particular with peroxide initiators or azo initiators in a temperature region from 50° C. to 130° C. During or after the polymerization, the methanol can be distilled out of the polymerization batch. In this way at least 95 percent of the methanol introduced in the mixture is recovered practically free of methyl methacrylate.

Technically produced mixtures of methanol and methyl methacrylate of the most different origins are adaptable to separation by the preparation of copolymers, soluble in organic solvents and particularly in petroleum oils and containing methyl methacrylate as a comonomer. The composition of the methanolmethyl methacrylate mixtures can vary within wide limits, for example from 10 to 95 percent by weight of methanol.

As organic solvents for carrying out the invention, essentially hydrocarbons come into consideration, the boiling points of which are above the boiling point of methanol (b.p. 64.7° C. at 1013 mbar). Advantageously, such solvents are used which do not form an azeotrope with methanol. (*Azeotropic Data-III*, Advances in Chemistry Series 116, American Chemical Society, Washington, D.C. 1973, pages 82 and 83). Among these are aromatic and aliphatic hydrocarbon such as ethylbenzene, the xylenes, cumene, and decane, undecane, and above all petroleum oils as aliphatic hydrocarbons, as known for the preparation of lubricating oil additives in the above-mentioned state of the art.

The solution polymers obtained according to the method of the invention meet the requirements set in DIN 51 382 or MIL H 5606 for use as viscosity index improvers.

A better understanding of the present invention and of its many advantages will be had from the following specific examples, given by way of illustration.

EXAMPLE 1

The following mixture is put into a 2 liter four-necked flask equipped with a stirrer, thermometer, and reflux condenser:

451.18 g of the methacrylic acid ester of a $C_{12}$–$C_{15}$-alcohol mixture containing 23 percent of branched alcohols;

17.40 g of N-dimethylaminopropylmethacrylamide;

82.22 g of an azeotrope of methyl methacrylate/methyl alcohol in a weight ratio=35/65; and 407.00 g of petroleum oil ($\eta_{100°\ C.}=3.9$ mm$^2$/S).

After solution of the components, polymerization is started at 72° C. with 1.00 g of tert.-butylperpivalate. The temperature remains constant at 72° C. during the polymerization because of the methanol reflux. Three hours after the start of polymerization, 1.00 g of tert.-butylperpivalate is added. The total polymerization time is 8 hours. After conclusion of the polymerization, the batch is diluted with 339.15 g of petroleum oil ($\eta_{100°\ C.}=3.9$ mm$^2$/s).

Thereafter, the apparatus is equipped with a Liebig condenser instead of the reflux condenser and the methyl alcohol is distilled off within an hour at a temperature of the reaction mixture of 80°–95° C.

A yellowish clear viscous solution is obtained.
Polymer content=40 percent by weight;
Viscosity (100° C., 40% by weight)=990 mm$^2$/s;
Viscosity (100° C., 40% by weight in petroleum oil with $\eta_{100°\ C.}=5.4$ mm$^2$/s)=15.7 mm$^2$/s;
SSI[1] (4% by weight in petroleum oil $\eta_{100°\ C.}=5.4$ mm$^2$/s)=46.

[1] Shear Stability Index: in this case the loss in thickening effect in percent when testing shear stability according to DIN 51 382.

EXAMPLE 2

The following mixture is put into a 2 liter four-necked flask with a stirrer, thermometer, reflux condenser, and dosage inlet:

300.0 g of petroleum oil ($\eta_{100°\ C.}=1.2$ mm$^2$/s);

28.97 g of the methacrylic acid ester of a $C_{12}$–$C_{15}$-alcohol mixture containing 23 percent of branched alcohols;

2.51 g of methyl methacrylate;

5.20 g of an azeotrope of methyl methacrylate/methyl alcohol in a weight ratio=35/65; and 6.36 g of tert.-butylperpivalate.

After solution of the components, the following mixture is added at 72° C. over a period of 210 minutes:

580.03 g of the methacrylic acid ester of a $C_{12}$–$C_{15}$-alcohol mixture containing 23 percent of branched alcohols;

50.21 g of methyl methacrylate;

104.18 g of an azeotrope of methyl methacrylate/methyl alcohol in a weight ratio=35/65; and 10.00 g of tert.-butylperpivalate.

2 hours after addition, 1.4 g of tert.-butylperpivalate are added.

Total polymerization time: 8 hours

After polymerization is over, the apparatus is restructured as described in Example 1 and the methyl alcohol is distilled off. A clear viscous solution is obtained.
Polymer content=70 percent by weight;
Viscosity (100° C., 70 weight percent)=950 mm$^2$/s;
Viscosity (40° C., 10.85 percent by weight in petroleum oil $\eta_{40°\ C.}=3.1$ mm$^2$/s)=14.1 mm$^2$/s; and
SSI[2] (10.85 percent by weight in petroleum oil with $\eta_{40°\ C.}=3.1$ mm$^2$/s)=18.

[2] Shear Stability Index: in this case, the loss in thickening effect in percent when testing shear stability according to MIL 5606 E.

What is claimed is:

1. A method for separating a mixture of methanol and methyl methacrylate formed in a technical process which comprises solution polymerizing the methyl methacrylate and recovering the methanol by distillation.

2. A method as in claim 1 wherein the methyl methacrylate is copolymerized.

3. A method as in claim 2 wherein the methyl methacrylate is copolymerized with at least one long-chain aliphatic $C_8$-$C_{20}$ alkyl ester of methacrylic acid as a comonomer.

4. A method as in claim 2 wherein said copolymerization is carried out as a solution polymerization in petroleum oil.

* * * * *